United States Patent [19]

Asahi et al.

[11] 4,396,719
[45] Aug. 2, 1983

[54] METHOD OF ESTIMATING THE INSULATION LIFE OF A RESIN INSULATOR

[75] Inventors: Mitsuyo Asahi, Kobe; Junzou Enomoto, Nishinomiya; Takao Tanaka, Kobe; Aiichiro Hashizume, Osaka, all of Japan

[73] Assignee: Mitsubishi Denki Kabushiki Kaisha, Hyogo, Japan

[21] Appl. No.: 253,765

[22] PCT Filed: Jul. 18, 1980

[86] PCT No.: PCT/JP80/00161
 § 371 Date: Mar. 25, 1981
 § 102(e) Date: Mar. 25, 1981

[87] PCT Pub. No.: WO81/00306
 PCT Pub. Date: Feb. 5, 1981

[30] Foreign Application Priority Data

Jul. 25, 1979 [JP] Japan .......................... 54-96284
Oct. 3, 1979 [JP] Japan .......................... 54-128355

[51] Int. Cl.³ .................................. G01N 33/44
[52] U.S. Cl. ................................ 436/85; 436/127; 436/144; 436/145; 436/155
[58] Field of Search ....... 23/230 PC, 230 M, 230 HC; M436/85, 136, 144, 145, 155

[56] References Cited

U.S. PATENT DOCUMENTS 3,868,221  2/1975  Howard et al. ............... 23/230 PC

FOREIGN PATENT DOCUMENTS 39-14748  7/1964  Japan ............................ 23/230 M

OTHER PUBLICATIONS

Electrochemical Lab. Tech. Bull. 33(9)–1969.
Hara et al.; C.A. 93:18601b.
Fedoseev et al.; C.A. 65:18685c.
C.A. 64:13370e.
C.A. 59:27b.

Primary Examiner—Michael S. Marcus
Attorney, Agent, or Firm—Sughrue, Mion, Zinn, Macpeak & Seas

[57] ABSTRACT

Either a monitoring resin piece associated with an electrical appliance or a resin piece forming a part of the insulating components of the electrical appliance is taken out after the electrical appliance has been operated for a suitable period of time, and either the ratio of the number of hydrogen atoms to the number of carbon atoms or the ratio of the number of oxygen atoms to the number of carbon atoms is measured to estimate the insulation life of the resin insulator of the electrical appliance.

4 Claims, 3 Drawing Figures

METHOD OF ESTIMATING THE INSULATION LIFE OF A RESIN INSULATOR

TECHNICAL FIELD

This invention is intended for estimating the insulation life of a resin insulator used in an electrical appliance to thereby prevent accidents attributed to the insufficient insulation thereof and for detecting when an insulating part or parts thereof should be replaced.

BACKGROUND ART

In general, solid, liquid and gas insulating materials are employed for insulating an electrical appliance. Of these insulating materials, the solid insulating materials are most extensively employed. Examples of the solid insulating materials are inorganic insulating materials, organic synthetic high molecular weight insulating materials and compounds thereof. After being used for many years, the insulating materials are subjected to electrical and mechanical deterioration and to thermal oxidation deterioration. As a result, the insulation characteristic of the electrical appliance is decreased, and finally dielectric breakdown is caused in the electrical appliance, which may result in the occurrence of an accident. If such an accident occurs then, a heavy loss is incurred and it requires much expense and time to repair and restore appliance to the former condition. Therefore, for accident prevention and security, there has been a strong demand for a method of detecting degradation in the insulation characteristic of an electrical appliance before dielectric breakdown occurs.

In order to meet this demand, a minute amount of deterioration product dissolved in the liquid in case of a liquid insulating material is detected with a highly sensitive gas analyzer to determine the degree of deterioration; and in case of a gas insulating material, a deterioration product mixed therein is detected with the gas analyzer to determine the degree of deterioration.

However, in case of a solid insulating material, unlike the above-described case, it is impossible to employ highly-sensitive gaseous deterioration product as the measure of deterioration, and therefore the deteriorated solid itself must be used for determining the degree of deterioration. On the other hand, a method in which the non-destructive electrical characteristics of an electrical appliance, such as for instance an insulation resistance, a dielectric characteristic and a partial discharge characteristic are measured to estimate the insulation life of the insulator of an electrical appliance, has been employed by way of trial. However, it should be noted that these characteristics do not satisfactorily correspond to the dielectric breakdown characterstic of the electrical appliance.

Since the insulation life of an insulator of an electrical appliance is determined from its dielectric breakdown voltage, in the present circumstance it is impossible to estimate the insulation life of insulator of an electrical appliance by the conventional method.

The inventors have conducted research on a method of detecting the behavior of the dielectric breakdown voltage of resin insulating materials used in electrical appliances. The breakdown voltage decreases with the lapse of operation time. As a result of the research, they have found that the ratio of the number of hydrogen atoms to the number of carbon atoms in the resin insulating materials varies with the time of use of the appliance and is satisfactorily corrspondent to the dielectric breakdown voltage decrease behavior.

DISCLOSURE OF THE INVENTION

This invention relates to a method of estimating the insulation life of resin insulator used in an electrical appliance. In the invention, a resin piece is removed from an electrical appliance, and the ratio of the number of hydrogen atoms to the number of carbon atoms in the resin piece is measured to thereby estimate the insulation life of the resin insulator. The resin piece may be sampled directly from an insulating component of the electrical appliance. Alternatively, a resin insulating material which is the same as or different from the insulating component of the electrical appliance may be mounted as a monitoring resin piece thereon, so that it can be removed when required.

The insulation life of the resin insulator in an electrical appliance can be similarly estimated by measuring the ratio of the number of oxygen atoms to the number of carbon atoms in the resin piece instead of the ratio of the number of hydrogen atoms to the number of carbon atoms.

An object of this invention is to provide a method of accurately estimating the insulation life of a resin insulator in an electrical appliance.

Another object of the invention is to provide a method of readily estimating the insulation life of a resin insulator in an electrical appliance.

A further object of the invention is to provide a method in which degradation of the insulation characteristic of an electrical appliance is detected before dielectric breakdown occurs in the appliance to thereby prevent the occurrence of an accident and to make it possible to carry out a suitable treatment such as the replacement of the insulators.

BEST MODE FOR CARRYING OUT THE INVENTION

Figure 1:
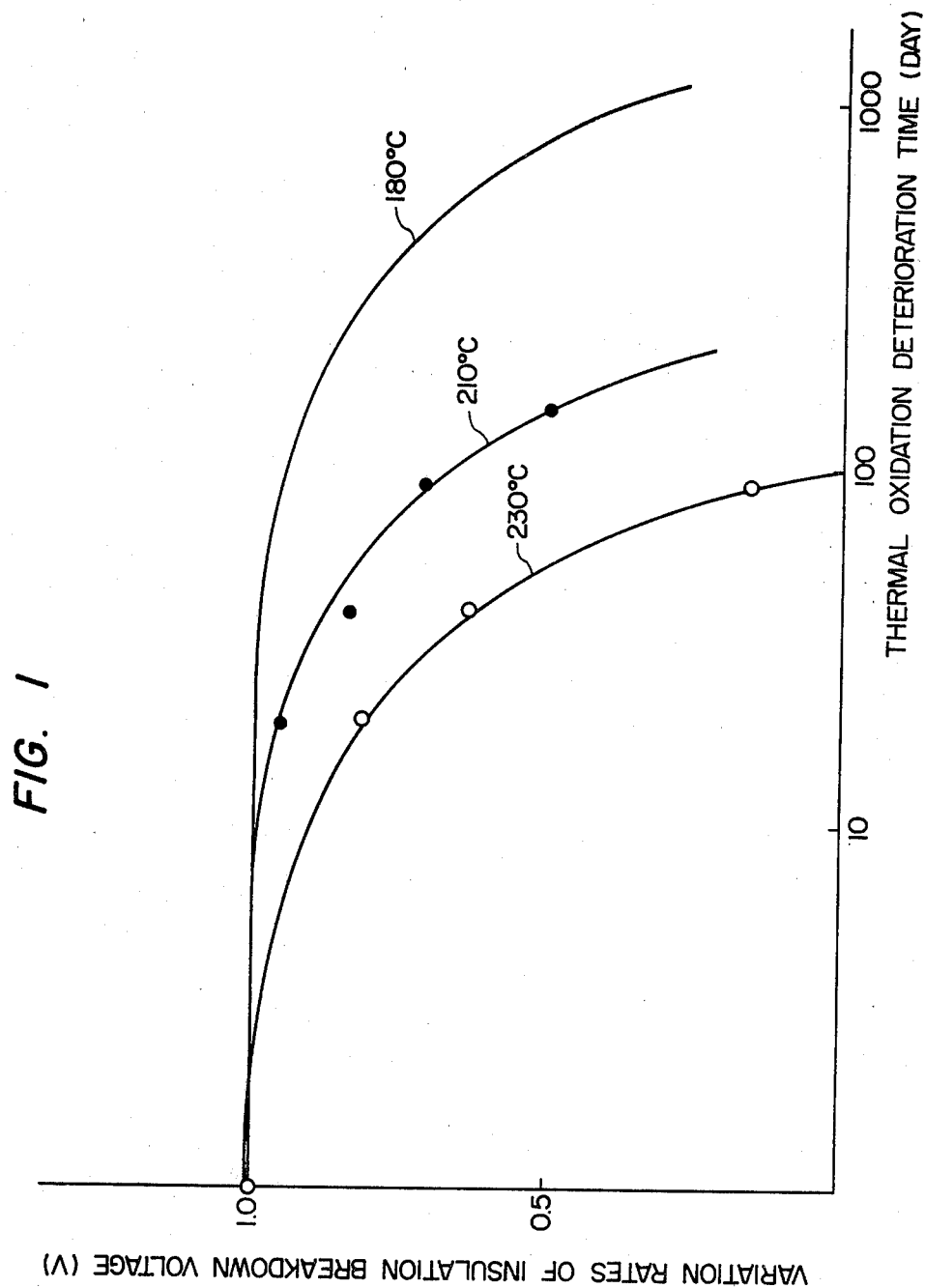
FIG. 1 is a characteristic diagram indicating the variation rates of the insulation breakdown voltage of a test bar with the thermal oxidation deterioration time.

The deterioration of insulation in an electrical appliance is mainly due to the thermal oxidation deterioration of its resin insulator. Synthetic organic high molecular weight substances forming a resin insulator are mainly made up of carbon atoms (C) and hydrogen atoms (H), and contain a small amount of oxygen atoms (O) and nitorogen atoms (N). With respect to the carbon and hydrogen atoms which are the main components of the resin insulator, the formation of double bonds and the replacement with oxygen atoms take place in the molecules by thermal oxidation deterioration, as a result of which the number of hydrogen atoms with respect to the number of carbon atoms is decreased.

The invention has been developed based on the above-described behavior of the resin insulator, and is intended to provide a method of estimating the degree of insulation deterioration of an insulator in an electrical appliance by utilizing this behavior.

In the method according to the invention, a suitable number of monitoring materials, namely, resin pieces which are prepared by using the same resin insulator as that employed in an electrical appliance to be measured are detachably mounted on the electrical appliance before the latter is operated, and the resin pieces are removed, for instance, one after another at suitable time intervals at suitable opportunities to measure the number of hydrogen atoms and the number of carbon atoms in each resin piece with an analyzer, to thereby obtain the ratio (H/C) of the former to the latter; or a model equal in insulation construction to an actual electrical appliance is used, so that the degree of insulation deterioration is estimated from the relation between the dielectric breakdown voltage decrease due to the thermal deterioration and the variation of the ratio (H/C) of the number of hydrogen atoms to the number of carbon atoms of the monitoring resin piece. Accordingly, degradation of the insulation characteristic can be detected before the dielectric breakdown occurs which makes it possible to prevent the occurrence of an accident and to carry out a suitable treatment such as for instance the replacement of the insulator.

Next, the invention will be concretely described with reference to its examples in which a typical epoxy resin is employed as a thermosetting resin which is used as an electrical appliance insulating resin.

EXAMPLE 1

A "Nomex paper" (produced by Du Pont Inc.) was wrapped around an iron core and was fixed by winding a glass tape thereon. Then, a low viscosity epoxy varnish was impregnated in vacuo thereinto and hardened in an electric furnace at 135° C., to obtain a coil test bar.

The above-describrd epoxy varnish was poured between two glass plates and was heated and hardened under the same manufacturing conditions as those in manufacturing the above-described test bar, to obtain a resin board 1 mm in thickness. Several monitoring resin pieces of 1×10×22 mm were cut off the resin board. The test bars and the resin pieces were inserted in electrical furnaces respectively at 180° C., 210° C. and 230° C. and were subjected to thermal oxidation deterioration.

After a certain period of time passed, five test bars were taken out of the furnaces, and their dielectric breakdown voltages were measured with 1 KV (A.C.) at room temperature in the air. At the same, the monitoring resin pieces were taken out of the furnaces and pulverized. A certain amount of monitoring resin pieces thus pulverized was analyzed with an element analyzer of CHN coder MT2 type manufactured by Kabushiki Kaisha Yanagimoto Seisakusho (Japan), to measure the weight of the hydrogen atoms and that of the carbon atoms. These weights were divided by the atomic weight 1.008 g of hydrogen and the atomic weight 12.011 g of carbon, to obtain the number of hydrogen atoms and the number of carbon atoms to thereby calculate the ratio (H/C) of the number of hydrogen atoms to the number of carbon atoms. The dielectric breakdown voltage has been standardized with the initial value.

The variations of the variation rate (v) of the test bar with thermal oxidation deterioration time are as indicated in FIG. 1 where v=dielectric breakdown voltage after thermal deterioration/initial dielectric breakdown voltage.

Figure 2:
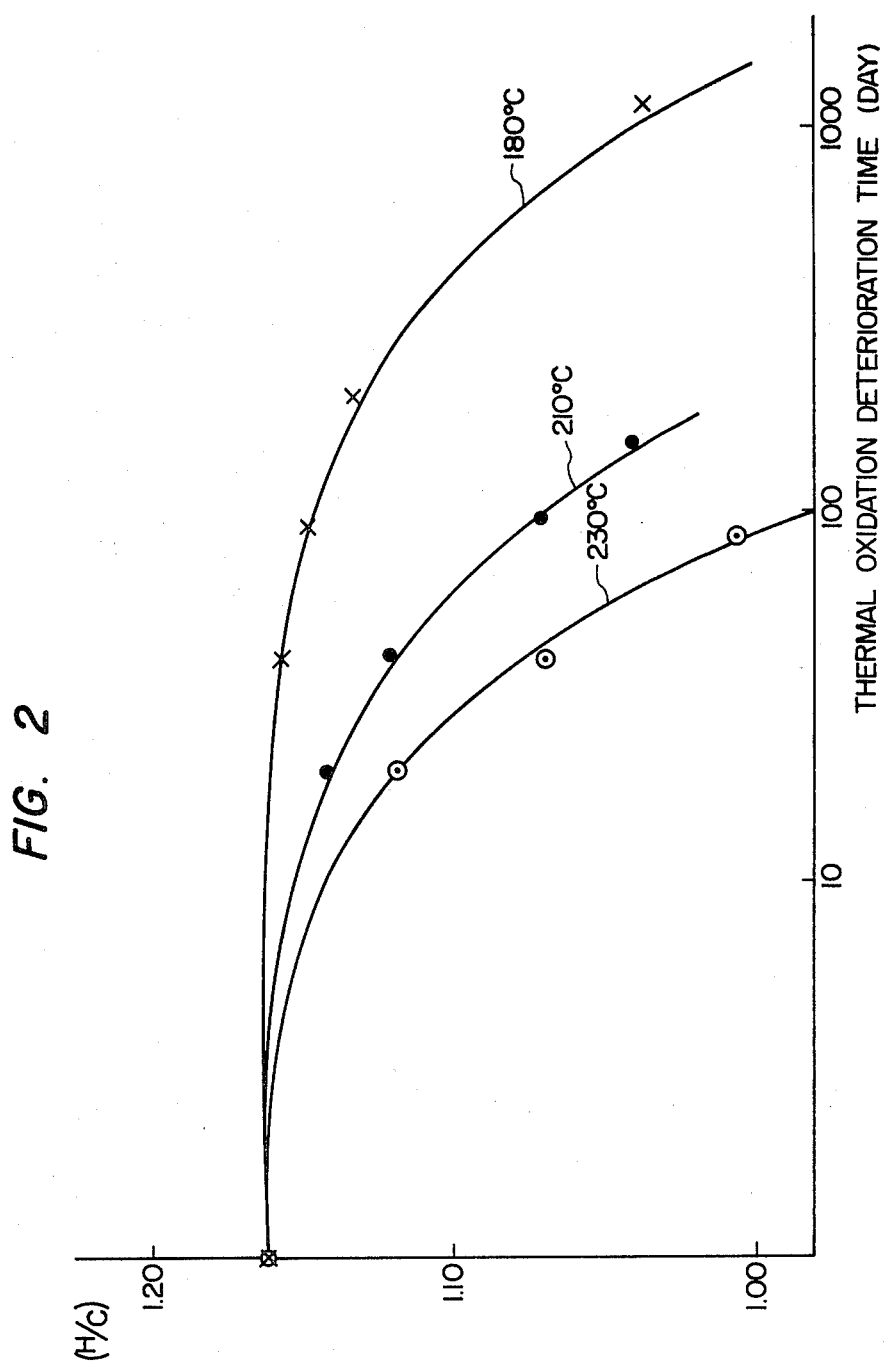
FIG. 2 is a characteristic diagram indicating the ratio of the number of hydrogen atoms to the number of carbon atoms in a monitoring resin piece with the thermal oxidation deterioration time.

The relations between the ratio (H/C) of the number of hydrogen atoms to the number of carbon atoms in the monitoring resin piece and the thermal oxidation deterioration time are as indicated in FIG. 2.

As is apparent from FIGS. 1 and 2, the variation of test bar dielectric breakdown voltage with thermal oxidation deterioration time is similar in tendency to the variation of the ratio (H/C) of the number of hydrogen atoms to the number of carbon atoms in the resin piece which is employed as the monitoring material, and the insulation deterioration of the test bar can be estimated from the ratio of the number of hydrogen atoms to the number of carbon atoms in the monitoring resin piece. If it is defined that the insulation life of the test bar ends when the dielectric breakdown voltage of the test bar is decreased to a half of the initial value, then when the test bars reach the end of their insulation lives at 180° C., 210° C. and 230° C., respectively, the ratio (H/C) of the number of hydrogen atoms to the number of carbon atoms is about 1.05 in each case. Thus, it can be understood that the ratios (H/C) are not dependent on the temperatures. Accordingly, the insulation life of an electrical appliance can be estimated from the ratio (H/C) of the number of hydrogen atoms to the number of carbon atoms in a monitoring resin piece which is assembled in the electrical appliance.

The method according to the invention utilizes elements, namely, carbon atoms and hydrogen atoms which are contained in all organic materials, and is based on their variations due to thermal oxidation deterioration. Therefore, it goes without saying that in addition to the epoxy resin employed in the above-described example, various thermosetting resins such as polyester resin, polyamide resin and polyamide imide resin, thermosoftening resins and other organic materials can be used as the monitoring resin piece.

The configuration of the monitoring resin piece is not limited to that defined in the above-described example; that is, it may be used in a desired form such as in the form of particles, powder or pellets. Furthermore, an inorganic filler or other fillers may be mixed with the resin.

For instance, in case of the stationary coil of an electric generator or an electric motor, the mounting position of the monitoring resin piece is on the surface of the coil, and in case of the rotary coil, the mounting position is below binding wires of the coil or below wedges of the coil.

In the above-described example, the monitoring resin pieces are mounted on the electric appliance in advance. However, if a small amount (for instance 2 mg) of resin is sampled from the surface of a resin insulator forming the insulating part of an electrical appliance to the extent that the insulation of the electrical appliance is not harmed, by measuring the ratio of the number of hydrogen atoms to the number of carbon atoms in the resin thus sampled, the insulation life may be estimated similarly as in the above-described example. Although the amount of resin sampled from the surface of the resin insulator in the electrical appliance is minute, to make sure it is acceptable, the part from which the resin has been sampled is repaired with resin which hardens at room temperature.

It is considered that the thermal oxidation deterioration of a resin insulator advances in such a manner that the carbon-carbon bonds in the molecules are cut, the hydrogen atoms separate so that double bonds are formed in the molecules, and the resulting double bonds are attacked by the oxygen in the air thereby fixing the oxygen atoms thereto. As a result of the thermal oxidation deterioration, the number of hydrogen atoms is decreased with respect to the number of carbon atoms, i.e. the number of oxygen atoms is increased with respect to the number of carbon atoms. Therefore, the insulation life can be estimated by measuring the ratio of the number of oxygen atoms to the number of carbon atoms instead of the ratio of the number of hydrogen atoms to the number of carbon atoms.

EXAMPLE 2

Figure 3:
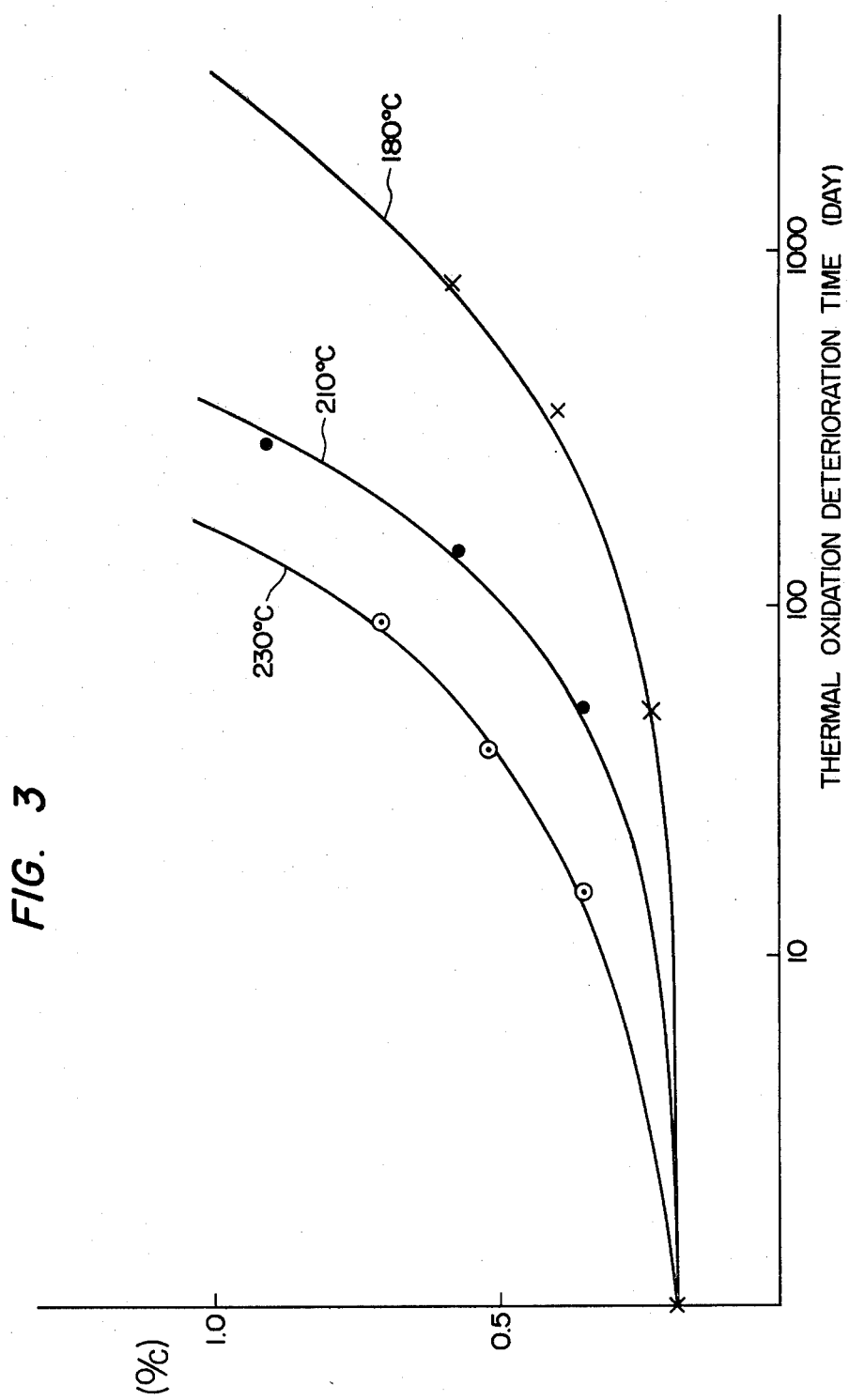
FIG. 3 is a characteristic diagram indicating the ratio of the number of oxygen atoms to the number of carbon atoms in a monitoring resin piece with the thermal oxidation deterioration time.

The monitoring resin pieces prepared in the example 1 were put in electric furnaces at 180° C., 210° C. and 230° C. and subjected to thermal oxidation deterioration. After a certain period of time passed, the monitoring resin pieces were taken out and pulverized. A predetermined amount of resin pieces thus pulverized was analyzed with the CHN coder MT2 type element analyzer to measure the weights of the hydrogen atoms and of the carbon atoms. The weight of the oxygen atoms was obtained by subtracting the sum of the weights of the hydrogen and carbon atoms from the weight of the resin used for the analyzation. The weight of the carbon atoms and the weight of the oxygen atoms were divided by the carbon atomic weight 12.011 g of the oxygen atomic weight 16.000 g to obtain the number of carbon atoms and the number of oxygen atoms, respectively, whereby the ratio (O/C) of the number of oxygen atoms to the number of carbon atoms were calculated. The relation between the ratio (O/C) of the number of oxygen atoms to the number of carbon atoms of the monitoring resin piece and the thermal oxidation deterioration time is as shown in FIG. 3.

The variation of the dielectric breakdown voltage of the test bar with thermal oxidation deterioration time of the example 1 is as shown in FIG. 1. As is apparent from a comparison of FIG. 1 with FIG. 3, the curves in FIG. 3 exhibit increasing variations in correspondence to the decreasing variations of the curves in FIG. 1. Thus, it can be understood that the insulation deterioration of the test bar (corresponding to the actual electrical appliance) can be estimated from the ratio of the monitoring resin piece. If it is defined that the insulation life of the test bar ends when the dielectric breakdown voltage of the test bar is decreased to ½ (half) of the initial value, when the test bars reach their insulation lives at 180° C., 210° C. and 230° C., respectively, the ratio (O/C) of the number of oxygen atoms to the number of carbon atoms of the monitoring resin piece is about 0.55 in each case. Accordingly, the insulation life of an electrical appliance can be estimated from the ratio (O/C) of the number of oxygen atoms to the number of carbon atoms of the monitoring resin piece which is mounted on the electrical appliance.

In the above-described method of measuring a ratio of the number of oxygen atoms to the number of carbon atoms, the monitoring resin piece is mounted on an electrical appliance in advance, and is then removed. However, it goes without saying that, in this case also, a small amount of resin may be sampled directly from a resin insulator forming an insulating part of the electrical appliance to measure the above-described ratio.

The resin material of the monitoring resin piece will be described in more detail. Of course, a resin insulator of the same insulating material employed in an electrical appliance to be tested can be employed as the resin material; however, this is not limitative. If a resin material is used which is correlative to the insulation deterioration characteristic of the insulating part of the electrical appliance under test and whose ratio of the number of hydrogen atoms or the number of oxygen atoms to the number of carbon atoms more greatly varies with the time of use of the electrical appliance than the resin insulator forming the insulating part, a monitoring resin piece which has a greater degree of increase or decrease of the measurement value and more sensitive to thermal oxidation deterioration can be obtained.

When the insulation of an electrical appliance deteriorates, in a resin insulator mainly forming the insulating part thereof, the carbon-carbon bonds in the molecules are cut because of the thermal oxidation deterioration or because double bonds are formed by oxidation and the oxygen atoms in the air which attack the resin are fixed in the molecules thereof to form carbonyl groups. As a result, the number of hydrogen atoms is decreased with respect to the number of carbon atoms, i.e. the number of oxygen atoms is increased with respect to the number of carbon atoms. Therefore, in case of a synthetic organic high molecular weight substance which is polyconjugated with increased ratio of double bond per molecule due to thermal oxidation deterioration, or in case of a synthetic high molecular weight substance in which it contains no oxygen atoms or contains a small number of oxygen atoms and the number of oxygen atoms is increased by thermal oxidation deterioration, or in case of a synthetic organic high molecular weight substance which meets both the above-described conditions, the number of hydrogen atoms is decreased with respect to the number of carbon atoms due to the thermal oxidation deterioration, and the degree of increase of the number of oxygen atoms with respect to the number of carbon atoms is increased.

Accordingly, suitable examples of the monitoring resin material are resins such as polyvinyl chloride and polyvinyl alcohol in which low molecular weight substances such as HCl and H₂O are eliminated by thermal oxidation, so that double bonds are formed in the molecules and polyconjugated; and polycarbonate or phenol resin which forms a structure of

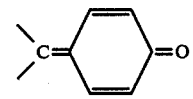

(quinometide) by thermal oxidation and makes polyconjugated.

As was described above, according to the invention, the insulation life of a resin insulator in an electrical appliance can be estimated with ease and with high accuracy.

INDUSTRIAL APPLICABILITY

This invention can be applied to the estimation of the insulation lives of any electrical appliance using resin insulating materials.

We claim:

1. A method of estimating the insulation life of a resin insulator in an electrical appliance, comprising the steps of:
providing at least one monitoring resin insulator sample in association with said appliance, said sample having the same insulating characteristics as said insulator in said appliance and said sample being made of a resin insulator material having a hydrogen to carbon atom ratio which varies with lifetime to a greater extent than the hydrogen to carbon atom ratio of said resin insulator in said appliance, and measuring the ratio of the hydrogen atoms to the carbon atoms in said sample, whereby said measured ratio provides an indication of the deterioration of the insulation breakdown voltage of said resin insulator.

2. The method of claim 1 wherein the step of providing at least one monitoring resin insulator sample comprises providing a multiplicity of said resin insulator samples in association with said appliance, and wherein the step of measuring comprises periodically measuring the hydrogen-carbon atom ratios of different ones of said samples to provide periodic estimates of the insulation life of said resin insulator.

3. A method of estimating the insulation life of a resin insulator in an electrical appliance, comprising the steps of:

providing at least one monitoring resin insulator sample in association with said appliance, said sample having the same insulating characteristics as said insulator in said appliance and said sample being made of a resin insulator material having a oxygen to carbon atom ratio which varies with lifetime to a greater extent than the oxygen to carbon atom ratio of said resin insulator in said appliance, and measuring the ratio of the oxygen atoms to the carbon atoms in said sample, whereby said measured ratio provides an indication of the deterioration of the insulation breakdown voltage of said resin insulator.

4. Themethod of claim 3 wherein the step of providing at least one monitoring resin insulator sample comprises providing a multiplicity of said resin insulator samples in association with said appliance, and wherein the step of measuring comprises periodically measuring the oxygen-carbon atom ratios of different ones of said samples to provide periodic estimates of the insulation life of said resin insulator.

* * * * *